(12) United States Patent  
Boedeker (10) Patent No.: US 8,998,804 B2
(45) Date of Patent: Apr. 7, 2015

(54) SUCTION CATHETER ASSEMBLY FOR A LARYNGOSCOPE

(75) Inventor: Benje Boedeker, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 771 days.

(21) Appl. No.: 12/611,459

(22) Filed: Nov. 3, 2009

(65) Prior Publication Data

US 2010/0121152 A1    May 13, 2010

Related U.S. Application Data

(60) Provisional application No. 61/198,963, filed on Nov. 12, 2008.

(51) Int. Cl.
| A61B 1/267 | (2006.01) |
| A61B 1/00  | (2006.01) |
| A61B 1/015 | (2006.01) |

(52) U.S. Cl.
CPC ............ *A61B 1/267* (2013.01); *A61B 1/00094* (2013.01); *A61B 1/0014* (2013.01); *A61B 1/015* (2013.01)

(58) Field of Classification Search
USPC .......................................... 600/184–199, 237
See application file for complete search history.

(56) References Cited

U.S. PATENT DOCUMENTS

| 4,565,187 | A  | * | 1/1986  | Soloway ...................... 600/193 |
| 4,901,708 | A  | * | 2/1990  | Lee ............................... 600/188 |
| 4,941,872 | A  | * | 7/1990  | Felix et al. ...................... 604/27 |
| 5,203,320 | A  | * | 4/1993  | Augustine ..................... 600/187 |
| 5,281,134 | A  | * | 1/1994  | Schultz ........................... 433/29 |
| 5,776,053 | A  | * | 7/1998  | Dragisic et al. .............. 600/195 |
| 5,800,344 | A  | * | 9/1998  | Wood et al. ................... 600/188 |
| 6,543,447 | B2 | * | 4/2003  | Pacey ....................... 128/200.26 |
| 6,672,305 | B2 | * | 1/2004  | Parker ...................... 128/200.26 |
| 7,174,889 | B2 | * | 2/2007  | Boedeker et al. ........ 128/200.26 |
| 7,608,040 | B1 | * | 10/2009 | Dunst ........................... 600/187 |
| 7,988,622 | B2 | * | 8/2011  | Achas Gandarias ......... 600/188 |
| 2005/0043590 | A1 | * | 2/2005 | Mazzei et al. ................ 600/188 |

* cited by examiner

*Primary Examiner* — Eduardo C Robert
*Assistant Examiner* — Steven Cotroneo
(74) *Attorney, Agent, or Firm* — Advent, LLP (57) ABSTRACT

A laryngoscope is provided with a suction catheter assembly that includes a catheter to supply suction for removal of fluids (e.g., blood, vomit, secretions, and so on) proximate to the distal end of the blade of the laryngoscope during intubation. A connector secures the catheter to the distal end of the blade. A retainer holds the catheter against the side of the blade.

18 Claims, 7 Drawing Sheets

SUCTION CATHETER ASSEMBLY FOR A LARYNGOSCOPE

CROSS-REFERENCE TO RELATED APPLICATION

The present application claims the benefit under 35 U.S.C. §119(e) of U.S. Provisional Application Ser. No. 61/198,963, filed Nov. 12, 2008, which is herein incorporated by reference in its entirety.

STATEMENT REGARDING FEDERALLY SPONSORED RESEARCH OR DEVELOPMENT

This invention was made with government support under Grant No. W81XWH-06-0019 awarded by the ARMY/MRMC. The federal government has certain rights in the invention.

BACKGROUND

Tracheal intubation involves the placement of a flexible plastic tube into the trachea to protect a patient's airway and provide a means of mechanical ventilation. A common tracheal intubation is orotracheal intubation, wherein an endotracheal tube is passed through the mouth, larynx, and vocal cords, into the trachea. A bulb is then inflated near the distal tip of the tube to help secure the tube in place and to protect the airway from blood, vomit, and secretions.

During orotracheal intubation, laryngoscopy is performed using a laryngoscope to obtain a view of the glottic opening for insertion of the endotracheal tube. Laryngoscopes typically include a blade that is inserted into the airway of a patient to allow the intubator to view the glottic opening through the patient's mouth. Video laryngoscopes employ an imaging device such as a small video camera, optical fibre, or the like, mounted to the blade to allow the intubator to view the glottic opening via a video monitor.

SUMMARY

Apparatus are described for supplying suction of fluids such as blood, vomit, secretions, and the like during orotracheal procedures such as laryngoscopy performed in orotracheal intubation. In an implementation, a laryngoscope is provided with a suction catheter assembly to supply suction for removal of fluids proximate to the distal end of the blade of the laryngoscope. The suction catheter assembly includes a catheter for supplying suction and a connector coupled to the distal end of the blade of the laryngoscope to attach the catheter to the blade. A retainer holds the catheter against the side of the blade.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The detailed description is described with reference to the accompanying figures. The use of the same reference numbers in different instances in the description and the figures may indicate similar or identical items.

DETAILED DESCRIPTION

Overview

During orotracheal intubation, fluids such as blood, vomit, secretions, and the like can obstruct the view of the glottic opening during laryngoscopy. The presence of fluids within the airway is especially challenging when performing intubations using a video laryngoscope because the imaging device of the laryngoscope can be occluded by such fluids. Consequently, it may be difficult to intubate the patient.

Accordingly, apparatus are described for supplying suction of fluids such as blood, vomit, secretions, and the like during orotracheal procedures such as laryngoscopy performed in orotracheal intubation. In an implementation, a laryngoscope is provided with a suction catheter assembly to supply suction for removal of fluids proximate to the distal end of the blade of the laryngoscope. The suction catheter assembly may also facilitate the injection of a fluid such as an anesthetic, an antibiotic, a topical drug, or other treatment, or a gas, such as oxygen, into the catheter for delivery into the airway of the patient. The suction catheter assembly includes a catheter for supplying suction and a connector coupled to the distal end of the blade to attach the catheter to the blade of the laryngoscope. The catheter is further attached to the blade at one or more points along the side of the blade by a retainer. In one or more embodiments, the laryngoscope blade may be formed to include the retainer as an integral part of the blade for attachment of the catheter to the blade. In other embodiments, the suction catheter assembly may be configured with a retainer that is independent of the laryngoscope blade to allow attachment of the suction catheter assembly to a variety of conventional laryngoscope blades as well as other devices (e.g., a tongue depressor, an endoscope device, and so on).

Example Implementations

Figure 1:
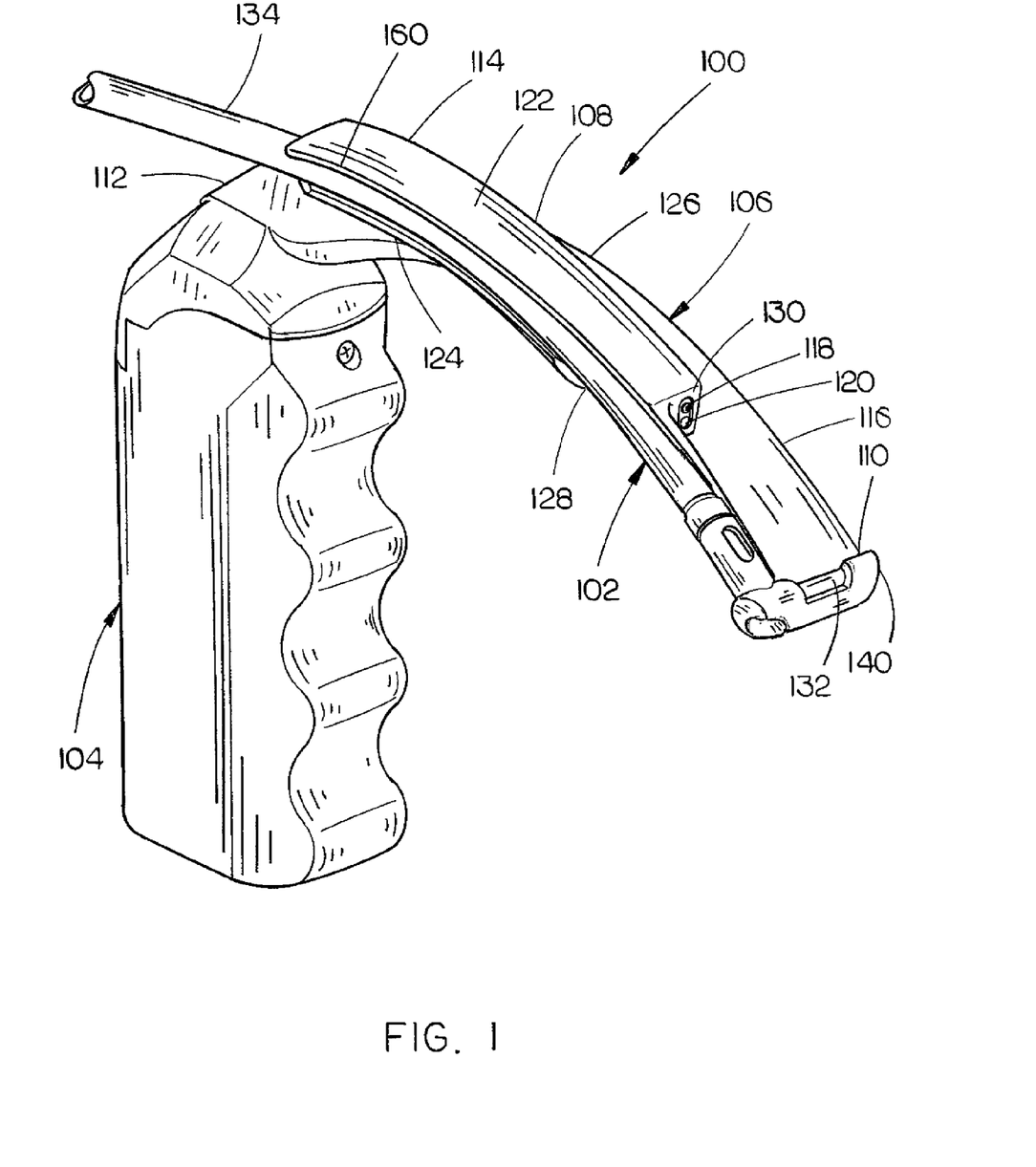
FIG. 1 is an isometric view illustrating a laryngoscope in an example implementation that is provided with a suction catheter assembly to supply suction of fluids during laryngoscopy.
Figure 2:
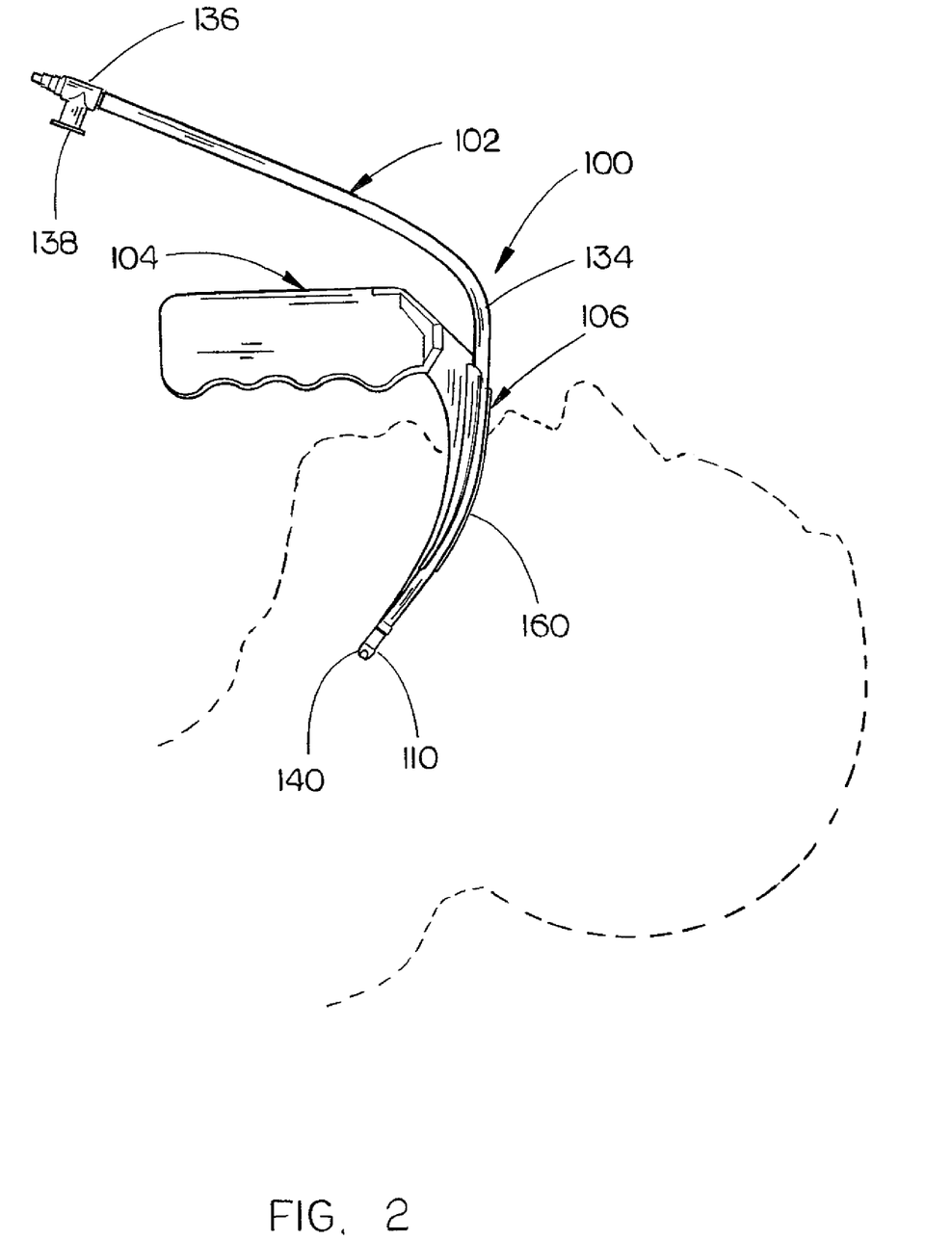
FIG. 2 is a side elevational view of the laryngoscope shown in FIG. 1, wherein the blade of the laryngoscope is inserted into the airway of a patient.
Figure 3:
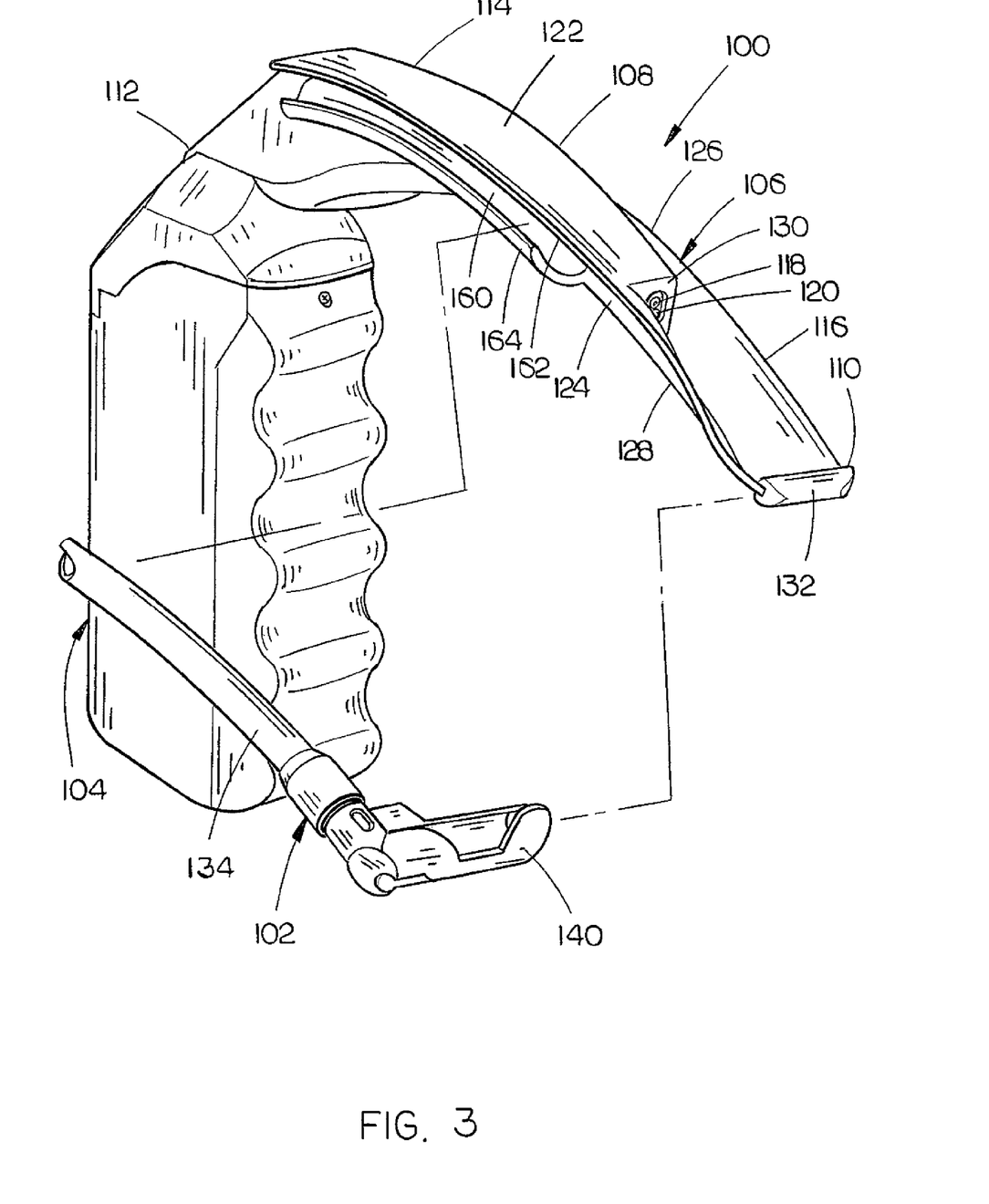
FIG. 3 is an exploded isometric view of the laryngoscope shown in FIG. 1, further illustrating the suction catheter assembly.

FIGS. 1 through 3 illustrate a laryngoscope 100 in an example implementation that is provided with a suction catheter assembly 102 to supply suction to evacuate fluids from a patient's airway during laryngoscopy. The laryngoscope 100 includes a handle assembly 104 and a blade 106. In the embodiment illustrated, the blade 106 generally comprises a curved blade such as a Macintosh blade, or the like. However, it is contemplated that other blade types may be provided. For example, in one or more embodiments the blade 106 may comprise a generally straight blade such as a Miller blade, a Robertshaw blade, a Wisconsin blade, or a Magill blade. Moreover, the blade 106 may be sized for use with patients of varied sizes. Thus, for example, the blade 106 may be sized for use with adults, children, infants, premature infants, and so on.

The blade 106 includes body 108, a distal end 110, and a proximal end 112. The body 108 includes an imaging device housing 114 and a flange 116 that extends from the housing 114 to distal end 110. The housing 114 is configured to hold an imaging device 118 for imaging the airway and, particularly, the glottic opening of a patient during intubation for display by a monitor (not shown). Example imaging devices 118 include digital video cameras (e.g., charge-coupled device (CCD) or complementary metal-oxide semiconductor (CMOS) camera-on-chip devices), fibre optic cameras, and so forth. The housing 114 may further be configured to hold a light source 120 for illuminating the area imaged by the imaging device 118.

In the implementation shown, the imaging device housing 114 is generally formed to include a top surface 122, a first side surface 124, a second side surface 126, a bottom surface 128, and a face 130, which holds the imaging device 118 and light source 120. The flange 116 projects from the body 108 along the bottom surface 128 and second side surface 126 to distal end 110. During intubation, the flange 116 and second side surface 126 may form a passage to aid in the insertion of the endotracheal tube through the glottic opening.

The distal end 110 of the blade 106 is spaced away from the face 130 of the housing 114, imaging device 118, and light source 120, and may be viewed as being positioned generally above the imaging device 118 and light source 120 when the blade 106 is inserted into the airway of a patient. The distal end 110 of the blade 106 includes a rod-shaped edge 132 that terminates the flange 116.

The proximal end 112 of the blade 106 is configured for attachment to the handle assembly 104. In embodiments, the blade 106 may be attached to the handle assembly 104 in a manner that generally precludes removal of the blade 106 in normal use. For example, the blade 106 and handle assembly 104 may be formed as an integral component, or the blade 106 may be attached to the handle assembly using one or more fasteners such as screws, bolts, rivets, and so on. In other embodiments, the blade 106 may be attached to the handle assembly 104 in a manner that facilitates easy replacement of one blade 106 with another. In this manner, a common handle assembly 104 may be used with interchangeable blades 106 of various types (e.g., Macintosh, Miller, etc.), sizes (e.g., adult, child, infant, etc.), and so on.

The suction catheter assembly 102 includes a catheter 134 that is configured to be coupled to a suction unit (e.g., aspirator) via an adapter 136 (shown in FIG. 2) to supply suction to evacuate fluids from a patient's airway proximate to the distal end 110 of the blade 106. In embodiments, the catheter 134 may have a size (e.g., internal diameter) sufficient to provide adequate suction for evacuation of fluids such as blood, vomit, secretions, tissue, and so forth without clogging. The catheter 134 may be formed of a polymer such as silicone, latex, a thermoplastic elastomer (e.g., polyvinyl chloride), and so on. In the implementation illustrated, the adapter 136 includes a thumb control valve 138 to allow the intubator to control the application of suction. However, an adapter 136 which does not employ a thumb control valve 138, or which employs another type of valve to control the application of suction, may be used.

In embodiments, the suction catheter assembly 102 may facilitate the injection of a fluid such as an anesthetic, an antibiotic, a topical drug, or other treatment into the catheter 134 for delivery into the airway of the patient proximate to the distal end 110 of the blade 106 (e.g., for delivery to the glottis). In such embodiments, the adapter 136 may be provided with a port that allows injection of a fluid into the catheter 134 using a syringe, or like device. Similarly, the suction catheter assembly 102 may facilitate the delivery of a gas, such as oxygen, into the airway of the patient proximate to the distal end 110 of the blade 106. The gas may be utilized for a variety of purposes such as insufflation during laryngoscopy, antifogging of the imaging device 118, and so forth. In such embodiments, the adaptor 136 may facilitate attachment of the catheter 134 to a source of the gas, such as an oxygen source, or the like.

Figure 4:
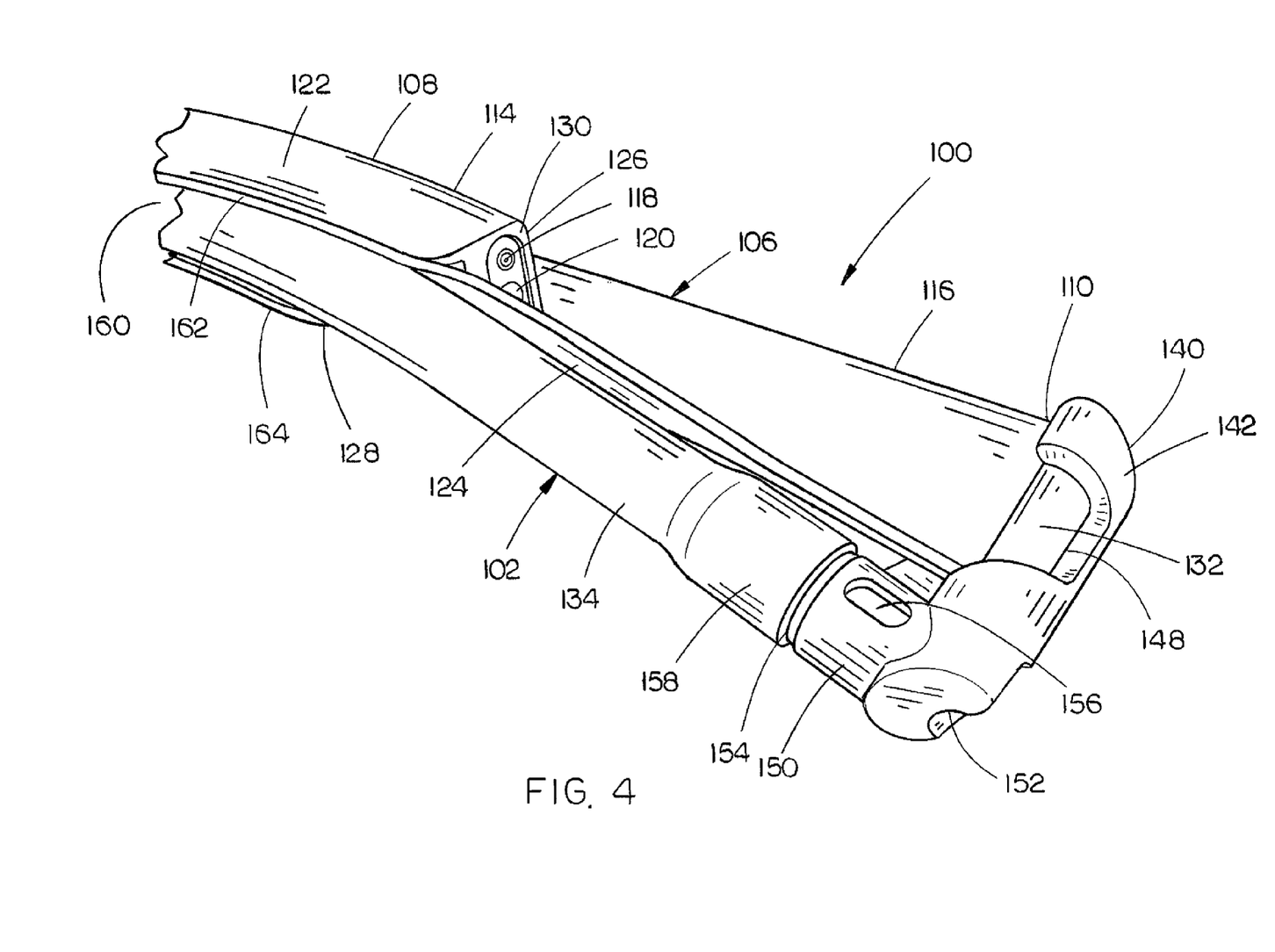
FIG. 4 is an isometric view of the laryngoscope shown in FIG. 1, further illustrating the distal end of the laryngoscope blade and the connector of the suction catheter assembly.
Figure 5:
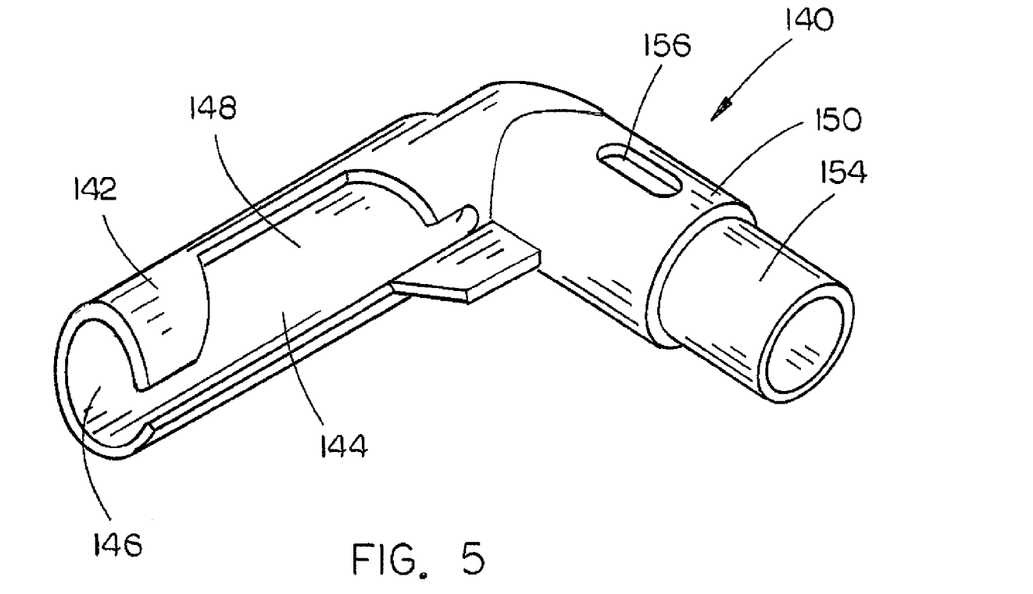
FIG. 5 is an isometric view of the connector of the suction catheter assembly shown in FIG. 1.
Figure 6:
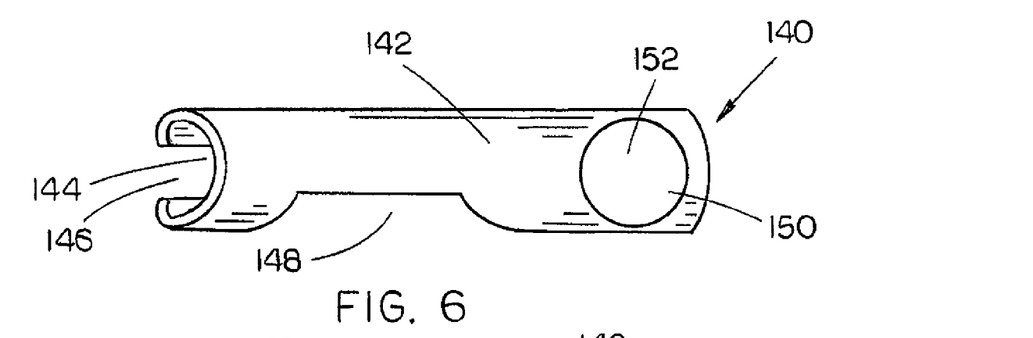
FIG. 6 is an end elevational view of the connector shown in FIG. 5.
Figure 7:
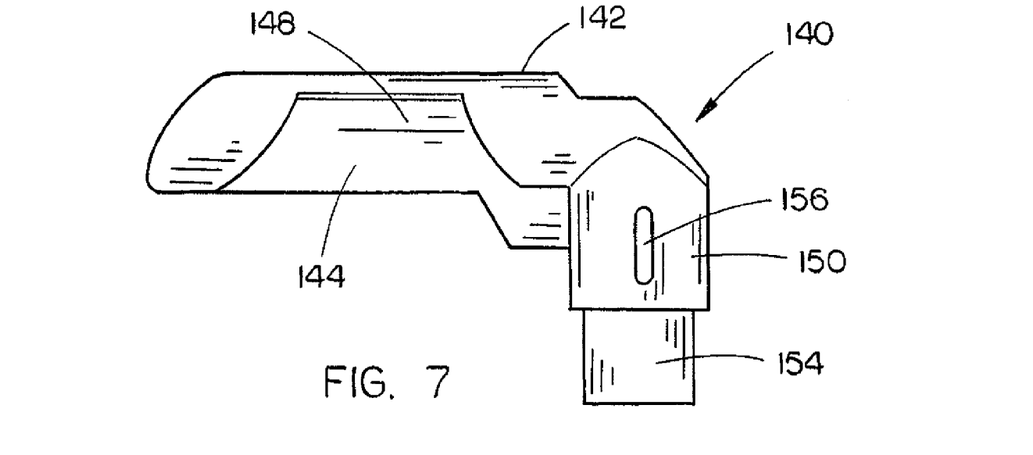
FIG. 7 is a top plan view of the connector shown in FIG. 5.

The suction catheter assembly 102 further comprises a connector 140 that couples the catheter 134 to the distal end 110 of the blade 106. As shown in FIGS. 3 through 5, the connector 140 includes a sleeve member 142 having a generally cylindrical channel 144 with an open end 146 that is configured to receive the rod-shaped edge 132 of the flange 116 (e.g., in a sliding engagement) to couple the connector 140 to the distal end 110 of the blade 106. In embodiments, the sleeve member 142 may include a recessed section 148 that reduces the profile of the connector 140 within the field of view of the imaging device 118. In this manner, the connector 140 may couple the catheter 134 to the distal end 110 of the blade 106 without significantly obscuring the area of the patient's airway (e.g., the glottic opening) imaged by the imaging device 118.

The connector 140 also includes a duct 150 having an orifice 152 and a catheter port 154. The catheter port 154 allows an end 158 of the catheter 134 to be coupled to the duct 150 so that fluids may be drawn into the catheter 134 through the duct 150 when suction is applied to the catheter 134. In embodiments, the duct 150 may include one or more vents 156 that prevent the formation of excess vacuum within the duct should the orifice 152 of the duct 150 become covered or obstructed. The vents 156 may thus help to prevent tissue of the mouth, larynx, vocal cords, and so on, from being unnecessarily drawn into the orifice 152 of the duct 150 by the applied suction, reducing the possibility of irritation during laryngoscopy.

In embodiments, the connector 140 may be formed of a polymer (with an appropriate plasticizer) such as Polyethylene (PE), Polyurethane, Polytetrafluoro-ethylene (PTFE), Polyethersulfone (PES), Polyethylene-terepthalate, and so on. However, other materials may be used.

The catheter 134 is attached to the blade 106 of the laryngoscope 100 at one or more points along the side of the blade 106 (e.g., alone first side surface 124) by a retainer 160. In embodiments, the blade 106 of the laryngoscope 100 may be formed to include the retainer 160 as an integral part of the blade 106. For example, in the implementation shown in FIGS. 1 through 7, the retainer 160 is illustrated as including a first clamping member 162 that extends from the first side surface 124 of the imaging device housing 114 along the top surface 122 and a second clamping member 164 that extends from the first side surface 124 adjacent to the first clamping member 162. As shown, the second clamping member 164 is at least substantially parallel to the first clamping member 162 and may be curved in cross-section to receive and retain the catheter 134.

In other embodiments, the suction catheter assembly 102 may be configured with a retainer 160 that is independent of the laryngoscope blade 106 to facilitate attachment of the suction catheter assembly 102 to the laryngoscope 100 without modification of the blade 106. For example, in the implementation shown in FIG. 8, the retainer 160 is illustrated as a separate component configured to attach the catheter 134 to the blade 106 of a laryngoscope 100. In such embodiments, the retainer 160 may have an elongated body 166 which may be formed of a polymer (with an appropriate plasticizer) such as Polyethylene (PE), Polyurethane, Polytetrafluoro-ethylene (PTFE), Polyethersulfone (PES), Polyethylene-terepthalate, and so on. As shown, the elongated body 166 may include a first clip 168 configured for attachment to a longitudinal edge 170 of a flange 116 of the laryngoscope blade 106 and a second clip 172 configured to receive and retain the catheter 134. Other configurations are possible. For example, the elongated body 166 may be formed as an integral part of the catheter 134. In such embodiments, first clip 168 may be molded or adhered to the side of the catheter 134 so that the second clip 172 is not utilized.

Figure 8:
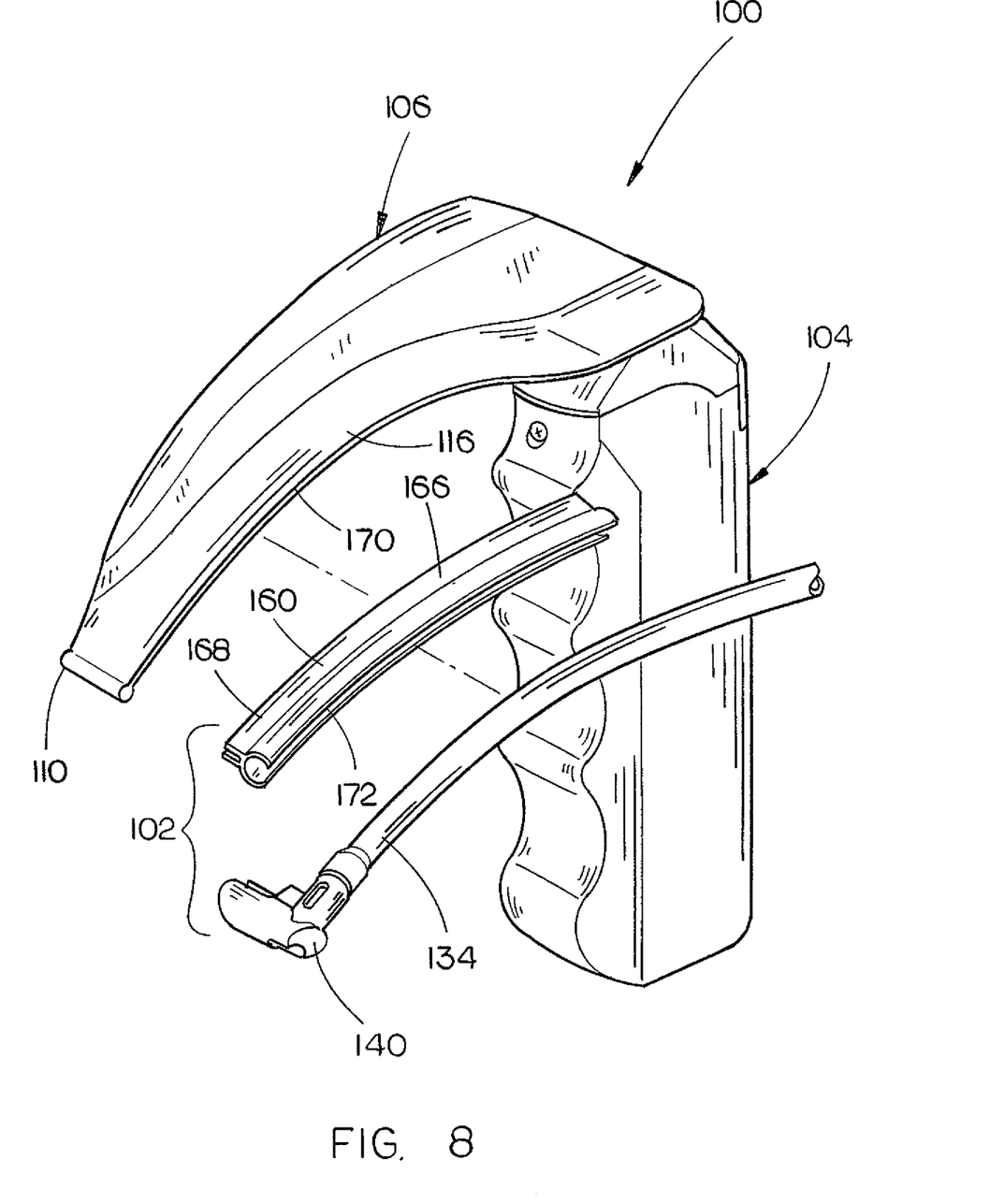
FIG. 8 is an isometric view illustrating a suction catheter assembly and laryngoscope in a second example implementation.
Figure 9:
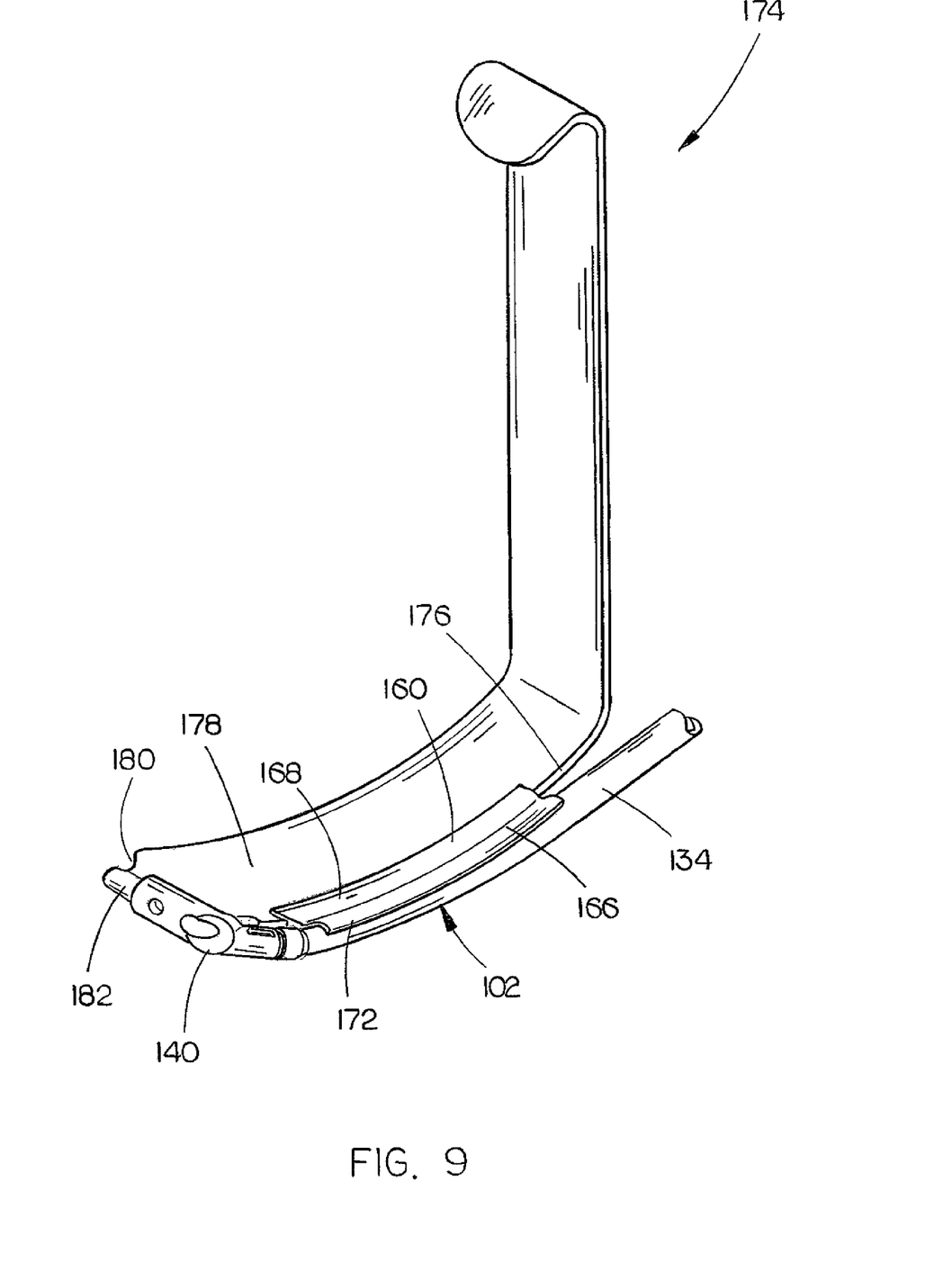
FIG. 9 is an isometric view illustrating attachment of the suction catheter assembly shown in FIG. 8 to a tongue retractor.

The retainer 160 illustrated in FIG. 8 facilitates attachment of the suction catheter assembly 102 to a variety of orotracheal devices. For example, FIG. 9 illustrates attachment of the suction catheter assembly 102 to a tongue retractor 174. As shown, the first clip 168 is coupled to a longitudinal edge 176 of the tongue retractor blade 178, while the second clip 172 receives and retains the catheter 134. The connector 140 is coupled to a distal end 180 of the tongue retractor blade 178. For example, like the distal end 110 of the laryngoscope blade 106, the distal end 180 of the tongue retractor blade 178 may comprise a rod-shaped edge 182. The sleeve member 142 of the connector 140 may receive the rod-shaped edge 182 (e.g., in a sliding engagement) to couple the connector 140 to the distal end 180 of the tongue retractor blade 178.

CONCLUSION

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A laryngoscope comprising:
   a handle assembly;
   a blade configured for insertion into the airway of a patient to facilitate viewing of the glottic opening during laryngoscopy, the blade including a proximal end coupled to the handle assembly and a distal end having a flange and a generally laterally disposed lip that terminates the flange;
   a catheter configured to supply suction; and
   a connector configured to be coupled to the distal end of the blade to attach the catheter to the blade, the connector including a channel configured for lateral sliding engagement with the lip so that the lip is received in the channel to secure in sliding engagement the connector to the blade and a duct having a port coupled to an end of the catheter for evacuation of fluids proximate to the distal end of the blade into the catheter via suction supplied by the catheter.

2. The laryngoscope as recited in claim 1, further comprising a retainer configured to hold the catheter against a side of the blade.

3. The laryngoscope as recited in claim 2, wherein the blade further comprises a body having a side surface including the retainer.

4. The laryngoscope as recited in claim 3, wherein the blade comprises an imaging device.

5. The laryngoscope as recited in claim 2, wherein the retainer comprises an elongated member having a first clip configured for connection to the blade and a second clip configured to receive the catheter.

6. The laryngoscope as recited in claim 1, wherein the catheter is further configured to facilitate delivery of at least one of a liquid or a gas into the airway proximate to the distal end of the blade.

7. The laryngoscope as recited in claim 1, wherein the lip comprises a generally rod-shaped edge.

8. The laryngoscope as recited in claim 7, wherein the channel of the connector is configured to laterally receive the generally rod-shaped edge.

9. A suction catheter assembly for an orotracheal device having a blade configured for insertion into the airway of a patient, the blade including a distal end having a flange and a generally laterally disposed lip that terminates the flange, the suction catheter assembly comprising:
   a catheter configured to supply suction; and
   a connector configured to be coupled to the distal end of the blade to attach the catheter to the blade, the connector including a channel configured for lateral sliding engagement with the lip so that the lip is received in the channel to secure in sliding engagement the connector to the blade and a duct having a port coupled to an end of the catheter for evacuation of fluids proximate to the distal end of the blade into the catheter via suction supplied by the catheter.

10. The suction catheter assembly as recited in claim 9, further comprising a retainer configured to attach the catheter to the blade.

11. The suction catheter assembly as recited in claim 10, wherein the retainer comprises an elongated member having a first clip configured for connection to the blade and a second clip configured to receive the catheter.

12. The suction catheter assembly as recited in claim 9, wherein the lip comprises a generally rod-shaped edge, and wherein the channel of the connector is configured to laterally receive the generally rod-shaped edge.

13. A laryngoscope assembly comprising:
   a laryngoscope comprising:
     a handle assembly; and
     a blade configured for insertion into the airway of a patient to facilitate viewing of the glottic opening during laryngoscopy, the blade including a proximal end coupled to the handle assembly and a distal end having a flange and a generally laterally disposed lip that terminates the flange; and
   a suction catheter assembly configured for attachment to the blade of the laryngoscope, the suction catheter assembly comprising:
     a catheter configured to supply suction;
     a connector configured to be coupled to the distal end of the blade to secure the catheter to the blade, the connector including a channel configured for lateral sliding engagement with the lip so that the lip is received in the channel to secure in sliding engagement the connector to the blade and a duct having a port coupled to an end of the catheter for evacuation of fluids proximate to the distal end of the blade into the catheter via suction supplied by the catheter; and
     a retainer configured to receive the catheter to hold the catheter against the blade.

14. The laryngoscope assembly as recited in claim 13, wherein the blade further comprises a body having a side surface including the retainer.

15. The laryngoscope assembly as recited in claim 13, wherein the retainer comprises an elongated member having a first clip configured for connection to the blade and a second clip configured to receive the catheter.

16. The laryngoscope assembly as recited in claim 13, wherein the catheter is further configured to facilitate delivery of at least one of a liquid or a gas into the airway proximate to the distal end of the blade.

17. The laryngoscope assembly as recited in claim 13, wherein the lip comprises a generally rod-shaped edge.

18. The laryngoscope assembly as recited in claim 17, wherein the channel of the connector is configured to laterally receive the generally rod-shaped edge.

\* \* \* \* \*